United States Patent [19]

van Niel

[11] Patent Number: 5,620,972

[45] Date of Patent: Apr. 15, 1997

[54] SUBSTITUTED BENZENE DERIVATIVES

[75] Inventor: Monique B. van Niel, Welwyn Garden City, England

[73] Assignee: Merck Sharp & Dohme Ltd., Hoddesdon, England

[21] Appl. No.: 492,558

[22] Filed: Jun. 20, 1995

[30] Foreign Application Priority Data

Jun. 29, 1994 [GB] United Kingdom ............. 9413090

[51] Int. Cl.⁶ .................. A61K 31/55; C07D 223/16
[52] U.S. Cl. ............................ 514/213; 540/523
[58] Field of Search ............. 540/523; 514/213

[56] References Cited

FOREIGN PATENT DOCUMENTS 04210967A 12/1989 Japan ................... 540/523

OTHER PUBLICATIONS

Bock, M. G. et al., Benzolactams As Non–Peptide Cholecystokinin Receptor Ligands, 1993, Bioorganic & Medicinal Chemistry Letters, vol. 3, No. 5, pp. 871–874.

*Primary Examiner*—Robert T. Bond
*Attorney, Agent, or Firm*—Robert J. North; Melvin Winokur

[57] ABSTRACT

Benzapines of the formula (I)

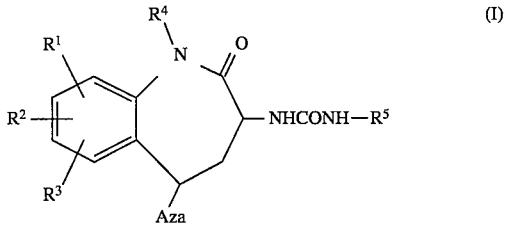

and salts and prodrugs thereof useful as CCK antagonists.

16 Claims, No Drawings

SUBSTITUTED BENZENE DERIVATIVES

This invention relates to benzazepine compounds which are useful as antagonists of cholecystokinin and gastrin receptors.

Cholecystokinins (CCK) and gastrin are structurally related peptides which exist in gastrointestinal tissue and in the central nervous system (see, V. Mutt, *Gastrointestinal Hormones*, G. B. J. Green, Ed., Raven Press, N.Y., p.169 and G. Nission, ibid. p.127).

Cholecystokinins include CCK-33, a neuropeptide of thirty-three amino acids in its originally isolated form (see, Mutt and Jorpes, *Biochem. J.* 125, 678 (1971)), its carboxylterminal octapeptide, CCK-8 (also a naturally-occurring neuropeptide and the minimum fully active sequence), and 39- and 12-amino acid forms. Gastrin occurs in 34-, 17- and 14-amino acid forms, with the minimum active sequence being the C-terminal tetrapeptide, Trp-Met-Asp-Phe-NH$_2$, which is the common structural element shared by both CCK and gastrim CCKs are believed to be physiological satiety hormones, thereby possibly playing an important role in appetite regulation (G. P. Smith, *Eating and Its Disorders*, A. J. Stunkard and E. Stellar, Eds, Raven Press, New York, 1984, p. 67), as well as stimulating colonic motility, gall bladder contraction, pancreatic enzyme secretion and inhibiting gastric emptying. They reportedly co-exist with dopamine in certain mid-brain neurons and thus may also play a role in the functioning of dopaminergic systems in the brain, in addition to serving as neurotransmitters in their own right (see A. J. Prange et al., "Peptides in the Central Nervous System", *Ann. Repts. Med. Chem* 17, 31, 33 [1982] and references cited therein; J. A. Williams, *Biomed Res.* 3 107 [1982]; and J. E. Morley, *Life Sci.* 30 479 [1982]).

The primary role of gastrin, on the other hand, appears to be stimulation of the secretion of water and electrolytes from the stomach and, as such, is involved in control of gastric acid and pepsin secretion. Other physiological effects of gastrin then include increased mucosal blood flow and increased antral motility. Rat studies have shown that gastrin has a positive trophic effect on the gastric mucosa, as evidenced by increased DNA, RNA and protein synthesis.

There are at least two subtypes of cholecystokinin receptors termed CCK-A and CCK-B (T. H. Moran et al., "Two brain cholecystokinin receptors: implications for behavioural actions", *Brain Res.*, 362, 175–79 [1986]). Both subtypes are found both in the periphery and in the central nervous system.

CCK and gastrin receptor antagonists have been disclosed for preventing and treating CCK-related and/or gastrin related disorders of the gastrointestinal (GI) and central nervous (CNS) systems of animals, especially mammals, and more especially those of humans. Just as there is some overlap in the biological activities of CCK and gastrin, antagonists also tend to have affinity for both CCK-B receptors and gastrin receptors. Other antagonists have activity at the CCK-A subtype.

Selective CCK antagonists are themselves useful in treating CCK-related disorders of appetite regulatory systems of animals as well as in potentiating and prolonging opiate-mediated analgesia [see P. L. Faris et al., *Science* 226, 1215 (1984)], thus having utility in the treatment of pain. CCK-B and CCK-A antagonists have also been shown to have a direct analgesic effect [M. F. O'Neill et al., *Brain Research*, 534 287 (1990)]. Selective CCK and gastrin antagonists are useful in the modulation of behaviour mediated by dopaminergic and serotonergic neuronal systems and thus have utility in the treatment of schizophrenia and depression (Rasmussen et. al., 1991, *Eur. J. Pharmacol.*, 209, 135–138; Woodruff et. al., 1991, *Neuropeptides*, 19, 45–46; Cervo et. al., 1988, *Eur. J. Pharmacol.*, 158, 53–59), as a palliative for gastrointestinal neoplasms, and in the treatment and prevention of gastrin-related disorders of the gastrointestinal system in humans and animals, such as peptic ulcers, Zollinger-Ellison syndrome, antral G cell hyperplasia and other conditions in which reduced gastrin activity is of therapeutic value, see e.g. U.S. Pat. No. 4,820,834. Certain CCK antagonists are useful anxiolytic agents and can be used in the treatment of panic and anxiety disorders.

CCK has been reported to evoke the release of stress hormones such as adrenocorticotrophic hormone, β-endorphin, vasopressin and oxytocin, CCK may function as a mediator of responses to stress and as part of the arousal system. CCK-A receptors are now known to be present in a number of areas of the CNS and may be involved in modulating any of the above.

CCK may be involved in the regulation of stress and its relationship with drug abuse e.g. alleviation of the benzodiazepine withdrawal syndrome (Singh et. al., 1992, *Br. J. Pharmacol.*, 105, 8–10) and neuroadaptive processes.

Since CCK and gastrin also have trophic effects on certain tumours [K. Okyama, *Hokkaido J. Med. Sci.*, 206–216 (1985)], antagonists of CCK and gastrin are useful in treating these tumours [see, R. D. Beauchamp et al., *Ann. Surg.*, 202, 203 (1985)].

In the light of discussion in C. Xu et al., *Peptides*, 8, 1987, 769–772, CCK antagonists may also be effective in neuroprotection.

CCK receptor antagonists have been found to inhibit the contractfie effects of CCK on iris sphincter and ciliary muscles of monkey and human eyes (Eur. J. Pharmacol., 211(2), 183–187; A. Bill et al., Acta Physiol. Scand., 138, 479–485 [1990]), thus having utility in inducing miosis for therapeutic purposes.

A class of benzodiazepine antagonist compounds has been reported which binds selectively to brain CCK (CCK-B and CCK-A) and gastrin receptors [see M. Bock et al.,*J. Med Chem.*, 32, 13–16 (1989)].

Bioorganic and Medicinal Chemistry Letters, Vol. 3, No. 5, pages 871 to 874, 1993 describes a series of 1,3-substituted benzazepines as CCK receptor ligands, and investigates the CCK receptor selectivity displayed by modifying the N-1 and C-3 side chains. There is no disclosure in that document of substitution at the 5-position of the subject benzazepine compounds.

JP 042 10967 discloses 1,2,4,5-tetra:hydro-3H-2-benzazepin-3-one derivatives which possess apomorphine enhancing, anti-convulsive and CCK antagonistic activity.

The present invention provides benzazepine compounds of formula (I), or a salt or prodrug thereof:

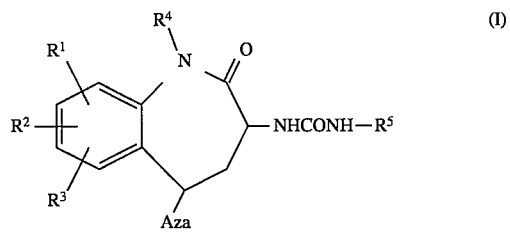

wherein:
(a) R$^1$ represents hydrogen, halogen, cyano, trifluoromethyl, nitro, —OR$^a$, —SR$^a$, —SOR$^a$, —SO$_2$R$^a$, —SO$_2$NR$^a$R$^b$, —NR$^a$R$^b$, —NR$^a$COR$^b$, —NR$^a$CO$_2$R$^b$, —COR$^a$, —CO$_2$R$^a$, —CONR$^a$R$^b$, or a hydrocarbon group comprising a straight chained, branched or cyclic group each containing up to 9 carbon atoms;

wherein R$^a$ and R$^b$ independently represent hydrogen, or a hydrocarbon group comprising a straight chained, branched or cyclic group each containing up to 9 carbon atoms;

(b) R$^2$ represents hydrogen, halogen or trifluoromethyl;

(c) R$^3$ represents hydrogen or halogen;

(d) R$^4$ represents hydrogen, an aliphatic group of up to 6 carbon atoms, a cycloaliphatic group of 3 to 6 carbon atoms, (CH$_2$)$_q$ imidazolyl, (CH$_2$)$_q$ tetrazolyl, (CH$_2$)$_q$triazolyl, where q is 1, 2 or 3;

(e) R$^5$ represents an optionally substituted aryl or heteroaryl; and (f) Aza represents an optionally substituted nitrogen containing moiety which is a cyclic or bicyclic group optionally containing 1, 2 or 3 additional heteroatoms, or is an acyclic group, said moiety containing up to 26 carbon atoms.

The term "halogen" as used herein includes fluorine, chlorine, bromine, and iodine.

The term "hydrocarbon group" as used herein with reference to R$^1$, R$^a$ and R$^b$ includes alkyl, alkenyl, alkynyl, cycloalkyl, alkyl, aryl, aryl-alkyl, aryl-alkenyl and aryl-alkynyl.

Suitable alkyl groups include straight-chained and branched alkyl groups containing from 1 to 6 carbon atoms. Typical examples include methyl and ethyl groups, and straight-chained or branched propyl and butyl groups. Particular alkyl groups are methyl, ethyl and t-butyl.

Suitable alkenyl groups include straight- chained and branched alkenyl groups containing from 2 to 6 carbon atoms. Typical examples include vinyl and allyl groups.

Suitable alkynyl groups include straight-chained and branched alkynyl groups containing from 2 to 6 carbon atoms. Typical examples include ethynyl and propynyl groups.

Suitable cycloalkyl groups include groups containing from 3 to 7 carbon atoms. Particular cycloalkyl groups are cyclopropyl and cyclohexyl.

A suitable aryl group is phenyl.

A particular aryl-alkyl group is benzyl.

A particular aryl-alkenyl group is phenylethenyl.

A particular aryl-alkynyl group is phenylethynyl.

With reference to R$^5$ suitable aryl groups include phenyl and naphthyl, especially phenyl, which groups may optionally be substituted by one or more substituents selected from hydrogen, halogen, cyano, trifluoromethyl, nitro, —OR$^a$, —SR$^a$, —SOR$^a$, —SO$_2$R$^a$, —SO$_2$NR$^a$R$^b$, —NR$^a$R$^b$, —NR$^a$COR$^b$, —NR$^a$CO$_2$R$^b$, —COR$^a$, —CO$_2$R$^a$, —CONR$^a$R$^b$, or a hydrocarbon group comprising a straight chained, branched or cyclic group each containing up to 9 carbon atoms, wherein R$^a$ and R$^b$ independently represent hydrogen, or a hydrocarbon group comprising a straight chained, branched or cyclic group each containing up to 9 carbon atoms.

A particularly suitable heteroaryl group represented by R$^5$ is pyridyl, which may optionally be substituted by one or more substituents selected from hydrogen, halogen, cyano, trifluoromethyl, nitro, —OR$^a$, —SR$^a$, —SOR$^a$, —SO$_2$R$^a$, —SO$_2$NR$^a$R$^b$, —NR$^a$R$^b$, —NR$^a$COR$^b$, —NR$^a$CO$_2$R$^b$, —COR$^a$, —CO$_2$R$^a$, —CONR$^a$R$^b$, or a hydrocarbon group comprising a straight chained, branched or cyclic group each containing up to 9 carbon atoms, wherein R$^a$ and R$^b$ independently represent hydrogen, or a hydrocarbon group comprising a straight chained, branched or cyclic group each containing up to 9 carbon atoms.

Typically R$^1$ represents hydrogen, and a suitable combination of the substituents R$^1$, R$^2$ and R$^3$ is seen when each R$^1$, R$^2$ and R$^3$ independently represent hydrogen.

Aptly R$^4$ represents an aliphatic group of up to 6 carbon atoms, and frequently represents methyl.

Suitably R$^5$ represents an optionally substituted phenyl or pyridyl group. Typical substituents are described above, and suitably hydrocarbon substituents, such as at least one C$_{1-6}$ alkyl group are conveniently employed. Aptly R$^5$ represents a phenyl or pyridyl group substituted by methyl.

Alternatively R$^5$ can be represented by the group

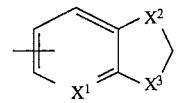

where X$^1$ represents CH or N, X$^2$ represents CH$_2$, and X$^3$ represents CH$_2$ or NR$^6$, where R$^6$ represents hydrogen or an aliphatic group of up to 6 carbon atoms, or X$^2$ and X$^3$ each represent oxygen.

Aptly the Aza moiety represents —NR$^c$R$^d$, wherein R$^c$R$^d$ independently represent hydrogen, a hydrocarbon group comprising a straight-chained, branched or cyclic group, an azacyclic or azabicyclic group, or R$^c$ and R$^d$ form the residue of an optionally substituted heterocycloalkyl, heterobicycloalkyl or heteroaryl. Alternatively, the Aza moiety can represent a carbon linked azacyclic or bicyclic group optionally containing 1, 2 or 3 additional heteroatoms.

In a first embodiment, R$^c$ and R$^d$ form the residue of an optionally substituted heterocycloalkyl, heterobicycloalkyl or heteroaryl, especially heterocyclo-alkyl.

The heterocycloalkyl of the Aza moiety, can be represented by:

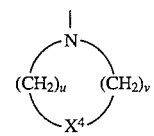

wherein

X$^4$ represents O, S, NR$^7$ or CH$_2$ where R$^7$ represents H, C$_{1-4}$alkyl, —CO$_2$R$^8$, —COR$^8$ or —SO$_2$R$^8$ where R$^8$ is C$_{1-6}$alkyl, optionally substituted phenyl or benzyl optionally substituted in the phenyl ring by one or more substituents, where the phenyl substituents are selected from C$_{1-4}$alkyl, C$_{1-4}$alkoxy, halo and trifluoromethyl;

v is 2, 3 or 4;

u is 1, 2, 3, 4, 5, 6, 7 or 8 when X is CH$_2$, or 2, 3, 4, 5, 6, 7 or 8 when X is O, S or NR$^7$.

Suitable heterocycloalkyl groups include:

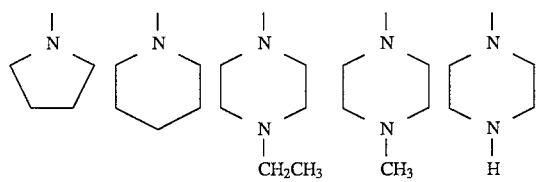

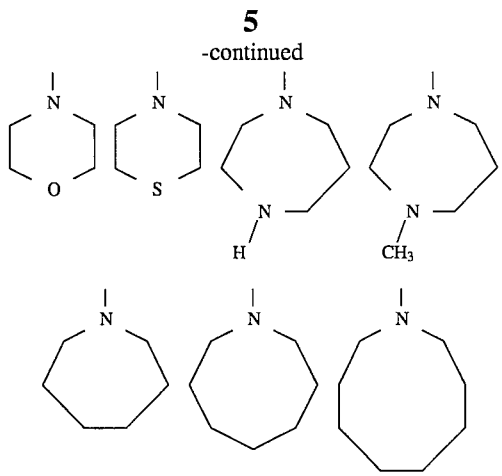

Preferred values of the Aza moiety are homopiperidine, N-methylpiperazine, hexamethyleneimine, heptamethyleneimine and octamethyleneimine, especially hexamethyleneimine.

In the case where $R^c$ and $R^d$ form the residue of an optionally substituted heterobicycloalkyl, the Aza moiety can represent an azabicyclic ring system which may be bridged, fused or spiro, preferably bridged. Examples of such azabicyclic ring systems include but are not limited to:

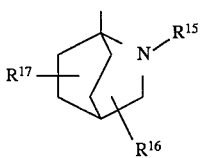

(A)

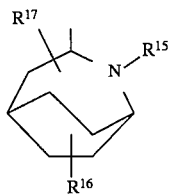

(B)

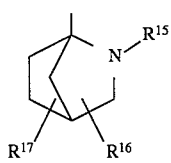

(C)

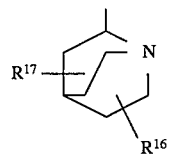

(D)

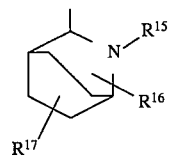

(E)

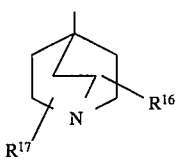

(F)

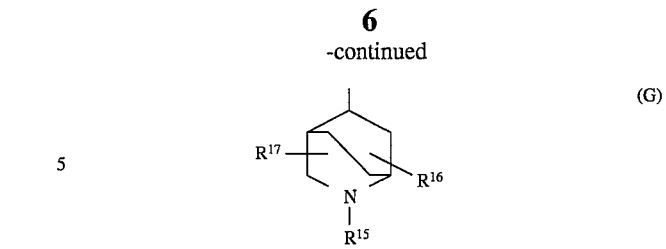

(G)

wherein $R^{15}$ represents H, $C_{1-4}$alkyl, optionally substituted phenyl or benzyl optionally substituted in the phenyl ring, where the phenyl substitutents are selected from $C_{1-4}$alkyl, $C_{1-4}$alkoxy, halo and trifluoromethyl; and $R^{16}$ and $R^{17}$ each represent H or $C_{1-4}$alkyl.

In a second embodiment the Aza moiety represents:

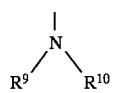

wherein
$R^9$ and $R^{10}$ each independently represents H, $C_{1-6}$alkyl optionally substituted by $NR^{11}R^{11'}$ where $R^{11}$ and $R^{11'}$ are hydrogen or $C_{1-4}$alkyl or an azacyclic or azabicyclic group, $C_{4-9}$cycloalkyl optionally substituted by one or more $C_{1-4}$alkyl groups, $C_{4-9}$cycloalkyl$C_{1-4}$alkyl optionally substituted in the cycloalkyl ring by one or more $C_{1-4}$alkyl groups, optionally substituted aryl, optionally substituted aryl$C_{1-6}$alkyl or azacyclic or azabicyclic groups.

A preferred compound according to the present invention is 1-(5-Azepan-1-yl-1-methyl-2-oxo-2,3,4,5-tetrahydro-1H-benzo[δ]azepin-3-yl)-3-m-tolyl-urea, or a salt or prodrug thereof.

The present invention includes within its scope prodrugs of the compounds of formula (I). In general, such prodrugs are functional derivatives of the compounds of formula (I) which are readily convertible in vivo into the required compound. Conventional procedures for the selection and preparation of suitable prodrug derivatives are described, for example, in "Design of Prodrugs", ed. H. Bundgaard, Elsevier, 1985.

Preferably the salts of the compounds of formula (I) are pharmaceutically acceptable, but non-pharmaceutically acceptable salts may be used for the preparation of pharmaceutically acceptable salts. The pharmaceutically acceptable salts of the compounds of formula (I). include the conventional non-toxic salts or the quaternary ammonium salts of the compounds from formula (I) formed, e.g., from nontoxic inorganic or organic salts. For example, such conventional non-toxic salts include those derived from inorganic acids such as hydrochloric, hydrobromic, sulphuric, sulphamic, phosphoric, nitric and the like; and the salts prepared from organic acids such as acetic, propionic, succinic, glycolic, steric, lactic, malic, tartaric, citric, ascorbic, palmoic, maleic, hydroxymaleic, phenylacetic, glutamic, benzoic, salicylic, sulphanilic, 2-acetoxy benzoic, fumaric, toluenesulphonic, methanesulphonic, ethane disulphonic, oxalic and isothionic. Preferred salts of the compounds according to the invention are hydrohalide, especially hydrochloride, salts.

The salts of the present invention can be synthesized from the compound of formula (I) which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The present invention also encompasses a pharmaceutical composition comprising a compound of formula (I), or a pharmaceutically acceptable salt or prodrug thereof, together with a pharmaceutically acceptable carrier, diluent, or excipient therefor.

The compounds of formula (I) and their salts and prodrugs, may be administered to animals, preferably to mammals, and most especially to a human subject either alone or, preferably, in combination with pharmaceutically acceptable carriers or diluents, optionally with known adjuvants, such as alum, in a pharmaceutical composition, according to standard pharmaceutical practice. The compounds can be administered orally, parenterally, including by intravenous, intramuscular, intraperitoneal or subcutaneous administration, or topically.

For oral use of an antagonist of CCK, according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavouring agents may be added.

For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

For topical administration, a compound of formula (I) may be formulated as, for example, a suspension, lotion, cream or ointment.

For topical administration, pharmaceutically acceptable carriers are, for example, water, mixtures of water and water-miscible solvents such as lower alkanols or arylalkanols, vegetable offs, polyalkylene glycols, petroleum based jelly, ethyl cellulose, ethyl oleate, carboxymethylcellulose, polyvinylpyrrolidone, isopropyl myristate and other conventionally-employed non-toxic, pharmaceutically acceptable organic and inorganic carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like.

The compounds of formula (I) antagonise CCK and/or gastrin and are useful for the treatment and prevention of disorders including central nervous system disorders wherein CCK and/or gastrin may be involved, and in a preferred embodiment, there is provided by the present invention, use of a compound of formula (I), or a salt or prodrug thereof, in the manufacture of a medicament for the treatment of a physiological disorder involving CCK and/or gastrin. Examples of such disease states include gastrointestinal diseases, including gastrointestinal ulcers, such as peptic and duodenal ulcers, irritable bowel syndrome, gastroesophagenal reflux disease or excess pancreatic or gastrin secretion, acute pancreatitis, or motility disorders; central nervous system disorders, including central nervous system disorders caused by CCK interaction with dopamine, serotonin and other monoamine neurotransmitters, such as neuroleptic disorders, tardive dyskinesia, Parkinson's disease, psychosis or Gilles de la Tourette syndrome; depression, such as depression resulting from organic disease, secondary to stress associated with personal loss, or idiopathic depression; schizophrenia; disorders of appetite regulatory systems; Zollinger-Ellison syndrome, antral and cell hyperplasia, or pain.

The compounds of formula (I) are particularly useful in the treatment or prevention of neurological disorders involving anxiety disorders and panic disorders, wherein CCK and/or gastrin is involved. Examples of such disorders include panic disorders, anxiety disorders, panic syndrome, anticipatory anxiety, phobic anxiety, panic anxiety, chronic anxiety and endogenous anxiety.

The compounds of formula (I) are also useful for directly inducing analgesia, opiate or non-opiate mediated, as well as anesthesia or loss of the sensation of pain.

The compounds of formula (I) may further be useful for preventing or treating the withdrawal response produced by chronic treatment or abuse of drugs or alcohol. Such drugs include, but are not limited to benzodiazepines, cocaine, alcohol and nicotine.

The compounds of formula (I) may further by useful in the treatment of stress and its relationship with drug abuse.

The compounds of formula (I) may further be useful in the treatment of oncologic disorders wherein CCK may be involved. Examples of such oncologic disorders include small cell adenocarcinomas and primary tumours of the central nervous system glial and neuronal cells. Examples of such adenocarcinomas and tumours include, but are not limited to, tumours of the lower oesophagus, stomach, intestine, colon and lung, including small cell lung carcinoma.

The compounds of formula (I) may also be useful as neuroprotective agents, for example, in the treatment and/or prevention of neurodegenerative disorders arising as a consequence of such pathological conditions as stroke, hypoglycaemia, cerebral palsy, transient cerebral ischaemic attack, cerebral ischaemia during cardiac pulmonary surgery or cardiac arrest, perinatal asphyxia, epilepsy, Huntington's chorea, Alzheimer's disease, Arnyotrophic Lateral Sclerosis, Parkinson's disease, Olivo-ponto-cerebellar atrophy, anoxia such as from drowning, spinal cord and head injury, and poisoning by neurotoxins, including environmental neurotoxins.

The compounds of formula (I) may further be used to induce miosis for therapeutic purposes after certain types of examination and intraocular surgery. An example of intraocular surgery would include cateract surgery with implantation of an artificial lens. The CCK antagonist compounds of this invention can be used to prevent miosis occuring in association with iritis, ureitis and trauma.

The present invention therefore provides a compound of formula (I) or a salt or prodrug thereof for use in the preparation of a medicament.

The present invention also provides a compound of formula (I) for use in therapy.

In a further or alternative embodiment the present invention provides a method for the treatment or prevention of a physiological disorder involving CCK and/or gastrin which method comprises administration to a patient in need thereof of a CCK and/or gastrin antagonising amount of a compound of formula (I).

When a compound according to formula (I) is used as an antagonist of CCK or gastrin in a human subject, the daily dosage will normally be determined by the prescibing physician with the dosage generally varying according to the age, weight, and response of the individual patient, as well as the severity of the patient's symptoms. However, in most instances, an effective daily dosage wll be in the range from about 0.005 mg/kg to about 100 mg/kg of body weight, and preferably, of from 0.05 mg/kg to about 50 mg/kg, such as from about 0.5 mg/kg to about 20 mg/kg of body weight, administered in single or divided doses. In some cases, however, it may be necessary to use dosages outside these limits. For example, animal experiments have indicated that doses as low as 1 ng may be effective.

In effective treatment of panic syndrome, panic disorder, anxiety disorder and the like, preferably about 0.05 mg/kg to about 0.5 mg/kg of CCK antagonist may be administered orally (p.o.), administered in single or divided doses per day (b.i.d.). Other routes of administration are also suitable.

For directly inducing analgesia, anaesthesia or loss of pain sensation, the effective dosage preferably ranges from about 100 ng/kg to about 1 mg/kg by systemic administration. Oral administration is an alternative route, as well as others.

In the treatment or irritable bowel syndrome, preferably about 0.1 to 10 mg/kg of CCK antagonist is administered orally (p.o.), administered in single or divided doses per day (b.i.d.). Other routes of administration are also suitable.

The use of a gastrin antagonist as a tumour palliative for gastrointestinal neoplasma with gastrin receptors, as a modulator of central nervous activity, treatment of Zollinger-Ellison syndrome, or in the treatment of peptic ulcer disease, an effective dosage of preferably about 0.1 to about 10 mg/kg administered one-to-four times daily is indicated.

For use as neuroprotective agents the effective dosage preferably ranges from about 0.5 mg/kg to about 20 mg/kg.

Because these compounds antagonise the function of CCK in animals, they may also be used as feed additives to increase the food intake of animals in daily dosage of preferably about 0.05 mg/kg to about 50 mg/kg of body weight.

There is further provided by the present invention an intermediate compound of the formula (IA):

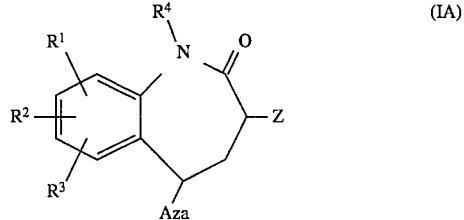

where Z represents $NH_2$, NHX where X is an amino protecting group, or —N=C=O, and $R^1$, $R^2$, $R^3$, $R^4$ and Aza are as hereinbefore defined.

The present invention also involves a process of preparing a compound of formula (I), or a salt or prodrug thereof, which comprises: reacting an intermediate of formula (IA) with a compound of formula (II):

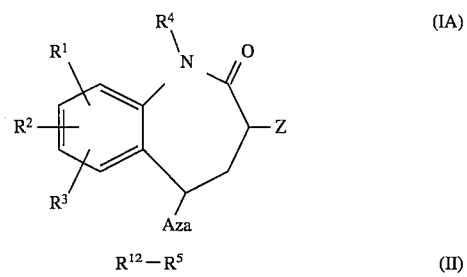

wherein:
(a) when Z represents $NH_2$ or NHX as defined above, $R^{12}$ represents —N=C=O; or
(b) when Z represents —N=C=O, $R^{12}$ represents $NH_2$ or NHX as defined above;
$R^1$, $R^2$, $R^3$, $R^4$, $R^5$ and Aza are as hereinbefore defined; and optionally converting a compound of formula (I) obtained into a salt or prodrug thereof.

Conventional amino protecting groups are described in *Protective Groups in Organic Chemistry*, ed. J. F. W. McOmie, Plenum Press, 1973; and T. W. Greene and P. G. M. Wutts, *Protective Groups in Organic Synthesis*, John Wiley & Sons, 1991. The protecting groups may be removed at a convenient subsequent stage using methods known from the art.

Suitable examples of amino-protecting groups include carboxylic acid groups such as acetyl, chloroacetyl, trifluoroacetyl, formyl, benzoyl, phthaloyl, phenylacetyl or pyridinecarbonyl; acid groups derived from carbonic acid such as ethoxycarbonyl, benzyloxycarbonyl, t-butoxycarbonyl, biphenylisopropoxycarbonyl, p-methylbenzyloxycarbonyl, p-nitrobenzyloxycarbonyl, p-bromobenzyloxycarbonyl, p-phenylazobenzyloxycarbonyl, p-(p'-methoxyphenylazo)-benzyloxycarbonyl or t-amyloxycarbonyl; acid groups derived from sulphonic acid, e.g. p-toluenesulphonic acid; and other groups such as methyl, benzyl, trityl,o-nitrophenylsulphenyl or benzylidene.

Preferred amino-protecting groups are methyl, benzyl, benzyloxycarbonyl and in particular t-butoxycarbonyl.

The removal of the amino-protecting group may be effected by an appropriate procedure known from the art, depending on the nature of the protecting group. For example, in the case where t-butoxycarbonyl is employed as the protecting group this can be removed by treatment with an acetate, such as ethyl acetate or the like, and a mineral acid such as hydrochloric acid.

The above is generally followed by reaction with $R^{12}$-$R^5$ as described above, in the presence of a base such as a tertiary amine, typically triethylamine. Aptly $R^{12}$-$R^5$ represents m-tolyl isocyanate.

Intermediates of formula (IA) can conveniently be prepared from compounds of the general formula (III):

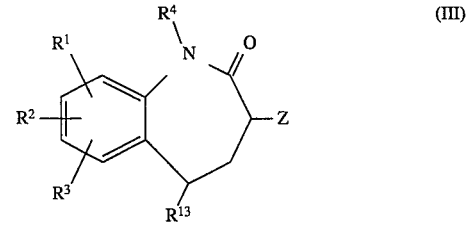

where $R^{13}$ represents an alkyl or aryl sulphonyloxy, such as mesylate or tosylate, by the reaction of the compound of formula (III) with an aza moiety, such as hexamethylenimine at a temperature in the range of 50° to 70° C.

Compounds of formula (III) are conveniently prepared from the corresponding hydroxy compounds of formula (IV):

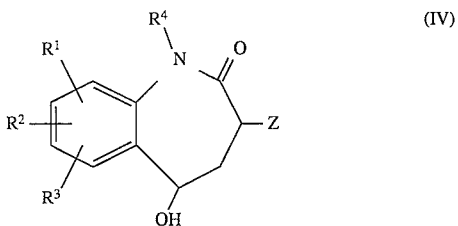

which are reacted with an aryl or alkyl sulphonyl halide, typically an aryl or alkyl sulphonyl chloride, in the presence of a base such as a tertiary amine, such as triethylamine and a suitable organic solvent, such as a halogenated hydrocarbon, for example, dichloromethane. The hydroxy compounds of formula (IV) are generally prepared from the corresponding carbonyl compounds of formula (V)

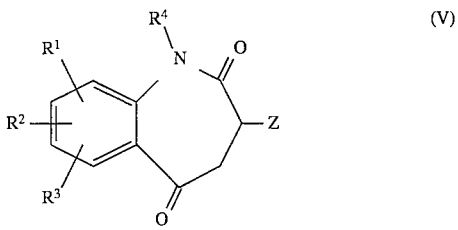

by reduction using a suitable catalyst, such as an alkali metal borohydride, for example sodium or lithium borohydride, in a suitable organic solvent, such as an alcohol, for example ethanol, typically at embient temperature.

Compounds of formula (V) are conveniently prepared from compounds of formula (VI):

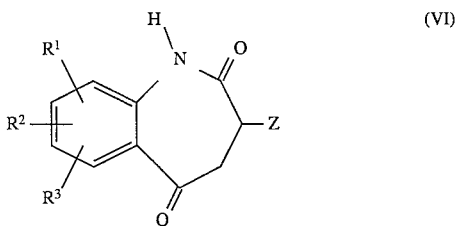

by reaction with $R^4$-Hal, where $R^4$ is as hereinbefore described and halogen includes fluorine, chlorine, bromine and iodine. The reaction is typically carried out in an anhydrous organic solvent, such as tetrahydrofuran.

Compounds of formula (VI) are readily available starting materials.

The novel compounds may be prepared in racemic form, or individual enantiomers may be prepared either by enantiospecific synthesis or by resolution of suitable intermediates prepared during the synthesis.

The novel compounds may for example, be prepared from enantiomerically pure starting materials, such as enantiomerically pure kynurenine, and the diastereomeric pairs formed when the C-5 centre is manipulated, can be separated by chromatographic or recrystallisation techniques. Alternatively suitable intermediates may be resolved into their component enantiomers by standard techniques such as HPLC using a chiral column, or formation of diastereomeric pairs by salt formulation with optically active acids, such as (−)-di-p-toluoyl-L-tartaric acid and/or (+)-di-p-toluoyl-D-tartaric acid followed by fractional crystallization, regeneration of the free base, and reintroduction of suitable protecting groups.

The present invention will now be illustrated by the following examples, which do not limit the scope of the invention in any way.

EXAMPLE 1 cis-1-(5-Azepan-1-yl-1-methyl-2-oxo-2,3,4,5-tetrahydro-1H-benzo[δ]azepin-3-yl)-3-m-tolyl-urea To a solution of 3-t-butyloxycarbonylamino-3,4-dihydro-1H-1-benzazepine-2,5-dione (500 mg, 1.72 mmol) in 25 ml anhydrous DMF was added cesium carbonate (562 mg) followed by iodomethane (215 µl). The reaction was stirred for one hour, diluted with ethyl acetate and then washed with water. The organic phase was separated, washed with brine, dried (MgSO$_4$) and concentrated to give a yellow solid. Tritiation with diethyl ether gave 3-t-butyloxycarbonylamino-1-methyl-3,4-dihydro-1H-1-benzazepine-2,5-dione as a colourless solid. 1H NMR (250 MHz, CDH$_3$) δ 7.64–7.50 (M, 2H) 7.38–7.24 (t, 1H) 7.20–7.60 (d, 1H,) 5.78–5.66 (br d, 1H,) 4.98–4.82 (M, 1H) 3.40 (s, 3H) 3.36–3.20 (dd, 2H) 2.98–2.80 (dd, 2H).

A solution of the product from above (800 mg, 2.63 mmol) in 40 ml ethanol was treated with sodium borohydride (119 mg). The reaction was stirred for two hours and then concentrated in vacuo. The residue was dissolved in CH$_2$Cl$_2$ and washed with water. The organic phase was separated, dried (MgSO$_4$) and concentrated. The residue was tritiated with diethyl ether-petroleum ether to give 3-t-butoxy carbonylamino-5-hydroxy-1-methyl-1,3,4,5-tetrahydro-1H-1-benzazepin-2-one as a colourless solid. (m/z (CI$^+$) 306)

To a solution of the alcohol from above (400 mg, 1.3 mmol) in 20 ml CH$_2$Cl$_2$ was added triethylamine (218 µl) and methanesulphonyl chloride (120 µl). The reaction was stirred for 3½ hours, concentrated and partitioned between ethyl acetate and 10% citric acid solution. The organic phase was dried, concentrated and tritiated with diethyl ether—petroleum ether to give methane sulfonic acid 3-amino-1-methyl-2-oxo-2,3,4,5-tetrahydro-1H-benzazepin-5-yl ester as a pale yellow solid. (m/z (CI$^+$) 385).

A solution of the mesylate from above (350 mg, 0.91 mmol) in 5 ml hexamethyleneimine was heated at 60° C. for 2 hours. The reaction was partitioned between CH$_2$Cl$_2$—water, and the organic phase dried (MgSO$_4$), concentrated, and purified by chromatography using ethyl acetate-CH$_2$Cl$_2$ as eluent to give 3-t-butyloxy carbonyl amino-5-azepan-1-yl-1-methyl-1,3,4,5-tetrahydro-benzo[b]azepin-2-one (m/z (EI$^+$) 387).

To a solution of the product from above (84 mg, 0.217 mmol) in 5 ml CH$_2$Cl$_2$ was added a saturated solution of HCl in ethyl acetate. The reaction was concentrated, redissolved in 5 ml CH$_2$Cl$_2$, and treated with triethylamine (91 µl) and then m-tolylisocyanate (34 µl). The reaction was stirred for one hour, washed with water, dried (MgSO$_4$), concentrated and purified by chromatography using CH$_2$Cl$_2$ and then 1:1 ethyl acetate-CH$_2$Cl$_2$ as eluent. The title compound was obtained as a colourless solid, following recrystallisation (m/z (CI$^+$) 420). $^1$H NMR (360 MHz, d$_6$-DMSO) δ 10.13 (br s, H), 9.00 (s, 1H), 7.65–7.61 (m, 2H), 7.51–7.49, (d, 7H), 7.43–7.39 (t, 1H), 7.17 (s, 1H), 7.12–7.04, (m, 2H), 6.71–6.69 (d, 2H), 4.93 (m, 1H), 4.24–4.20 (m, 1H), 3.47–3.40 (m, 1H), 3.33 (s, 3H), 3.17 (m, 1H), 2.91–2.88 (m, 2H) 2.65–2.60 (m, 1H) 2.36–2.28 (t, 1H) 2.21 (s, 3H), 1.84 (s, 2H), 1.70 (br s, 2H) 1.57–1.23 (m, 3H)

EXAMPLE 2 cis and trans 1-(5-Azepan-1-yl-1-methyl-2-oxo-2,3,4,5-tetrahydro-1H-benzo[δ]azepin-3-yl)-3-m-tolyl urea.

To a suspension of 3-t-butyloxycarbony(amino-1-methyl-3,4-dihydro-1H-1-benzazepine-2,5-dione (0.683 g, 2.24 mmol) (example 1) in titanium (IV) isopropoxide (0.8 ml) was added hexamethyleneimine (0.28 ml). Anhydrous THF (10 ml) was added and the resultant slurry was stirred for 2 h under a nitrogen atmosphere, to give a clear yellow solution. The reaction was diluted with ethanol (5 ml) and sodium cyanoborohydride (0.141 g) was added. The reaction was concentrated after 48 h, diluted with ethyl acetate-water, filtered through Celite, and the organic phase was separated, dried over MgSO$_4$ and concentrated. Purification by MPLC chromatography on silica gel gave 3-t-butyloxy carbonyl amino-5-azepan-1-yl-1-methyl-1,3,4,5-tetrahydro-benzo(δ)azepin-2-one as a mixture of diastereoisomers.

The products from above were converted to the title compounds using a similar procedure to that described for Example 1. Separation of the diastereomers was achieved by chromatography using 20% ethyl acetate-petroleum ether as eluent to give the product from Example 1 and trans 1-(5-azepan-1-yl-1-methyl)-2-oxo-2,3,4,5-tetrahydro-1H-benzo[δ]azepin-3-yl)-3-m-tolyl urea, as a colourless solid.

m.p. 182°–184° C. (methanol). (M/z CI 421). $^1$H NMR (360 MHz, d$_6$-DMSO) δ 1.5–1.7 (8H,m), 2.0–2.1 (1H,m), 2.21 (3H,s), 2.27–2.23 (1H, m), 2.69–2.74 (4H,m) 3.30 (3H,s), 3.69–3.74 (1H,m), 3.96–4.05 (1H,m), 6.51–6.53 (1H, 6.66–6.68 (1H,m), 7.01–7.07 (2H,m), 7.15 (1H,m), 7.31–7.36 (3H,m), 7.55–7.57 (1H,m), 8.24 (1H,s).

The relative stereochemistry of these products was assigned following nOe studies, and a single crystal x-ray structure was obtained for the trans—disastereoisomer

EXAMPLE 3

Biological Activity

The CCK-A and CCK-B antagonising activity of the compound described in Example 1 was evaluated using the assays described in published European patent application no. 0514133. The method essentially involves determining the concentration of the test compound required to displace 50% of the specific $^{125}$I-CCK from rat pancreas (CCK-A) or guinea pig brain (CCK-B), and was found to be 100 nM for CCK-A and 14 nM for CCK-B.

The corresponding figures for the compounds of Example 2 were about 650 nM and 6.9 nM for the 3R, 5R, 3S, 5S isomer and about 17 nM and 15.7 nM for the 3R, 5S, 3S, 5R isomer.

I claim:

1. A compound of formula (I), or a pharmaceutically acceptable salt thereof:

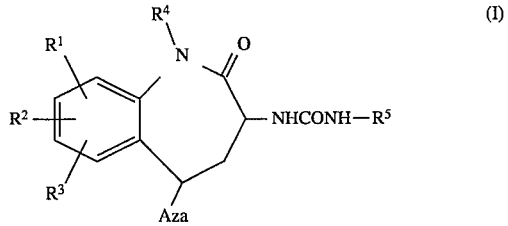

wherein:

(a) R$^1$ represents hydrogen, halogen, cyano, trifluoromethyl, nitro, —OR$^a$, —SR$^a$, —SOR$^a$, —SO$_2$R$^a$, —SO$_2$NR$^a$R$^b$, —NR$^a$R$^b$, —NR$^a$COR$^b$, —NR$^a$CO$_2$R$^b$, —COR$^a$, —CO$_2$R$^a$, —CONR$^a$R$^b$, or a hydrocarbon group comprising a straight chained, branched or cyclic group each containing up to 9 carbon atoms;

wherein R$^a$ and R$^b$ independently represent hydrogen, or a hydrocarbon group comprising a straight chained, branched or cyclic group each containing up to 9 carbon atoms;

(b) R$^2$ represents hydrogen, halogen or trifluoromethyl;

(c) R$^3$ represents hydrogen or halogen;

(d) R$^4$ represents hydrogen, an aliphatic group of up to 6 carbon atoms, a cycloaliphatic group of 3 to 6 carbon atoms, (CH$_2$)$_q$ imidazolyl, (CH$_2$)$_q$ tetrazolyl, (CH$_2$)$_q$triazolyl, where q is 1, 2 or 3;

(e) R$^5$ represents phenyl, naphthyl or pyridyl optionally substituted by one or more substituents selected from hydrogen, halogen, cyano, trifluoromethyl, nitro, —OR$^a$, —SR$^a$, —SOR$^a$, —SO$_2$R$^a$, —SO$_2$NR$^a$R$^b$, —NR$^a$R$^b$, —NR$^a$COR$^b$, —NR$^a$CO$_2$R$^b$, —COR$^a$, —CO$_2$R$^a$, —CONR$^a$R$^b$, or a hydrocarbon group comprising a straight chained, branched or cyclic group each containing up to 9 carbon atoms;

wherein R$^a$ and R$^b$ independently represent hydrogen, or a hydrocarbon group comprising a straight chained, branched or cyclic group each containing up to 9 carbon atoms, or R$^5$ represents a group

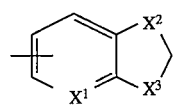

where X$^1$ represents CH or N, X$^2$ represents CH$_2$, X$^3$ represents CH$_2$ or NR$^6$, where R$^6$ represents hydrogen or an aliphatic group of up to 6 carbon atoms, or X$^2$ and X$^3$ each represent oxygen; and (f) Aza represents:
(i) a heterocyclic group of formula:

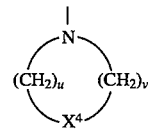

wherein:

X$^4$ represents O, S, NR$^7$ or CH$_2$, where R$^7$ represents H, C$_{1-4}$alkyl, —CO$_2$R$^8$, —COR$^8$ or —SO$_2$R$^8$ where R$^8$ is C$_{1-6}$alkyl, optionally substituted phenyl or benzyl optionally substituted in the phenyl ring by one or more substituents, where the phenyl substituents am selected from C$_{1-4}$alkyl, C$_{1-4}$alkoxy, halo and trifluoromethyl;

v is 2, 3 or 4;

u is 1, 2, 3, 4, 5, 6, 7 or 8 when X is CH$_2$, or 2, 3, 4, 5, 6, 7 or 8 when X is O, S or NR$^7$;

(ii) an azabicyclic group of formula:

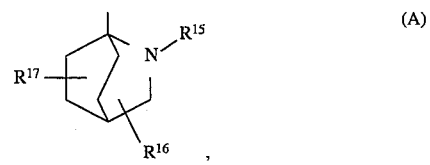

(A)

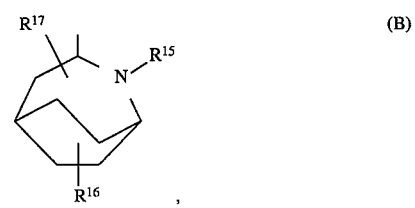

(B)

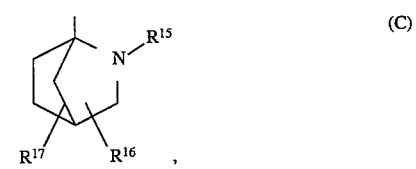

(C)

wherein $R^{15}$ represents H, $C_{1-4}$alkyl, optionally substituted phenyl or benzyl optionally substituted in the phenyl ring, where the phenyl substitutents are selected from $C_{1-4}$alkyl, $C_{1-4}$alkoxy, halo and trifluoromethyl; and $R^{16}$ and $R^{17}$ each represent H or $C_{1-4}$alkyl; or (iii)

wherein $R^9$ and $R^{10}$ each independently represents H, $C_{1-6}$alkyl optionally substituted by $NR^{11}R^{11'}$ where $R^{11}$ and $R^{11'}$ are hydrogen or $C_{1-4}$alkyl or a heterocyclic group which is as defined above with the exception that $X^4$ represents $NR^7$ or $CH_2$ or an azabicyclic group as defined above, $C_{4-9}$cycloalkyl optionally substituted by one or more $C_{1-4}$alkyl groups, $C_{4-9}$cycloalkyl$C_{1-4}$alkyl optionally substituted in the cycloalkyl ring by one or more $C_{1-4}$alkyl groups, optionally substituted phenyl, optionally substituted phenyl$C_{1-6}$alkyl or a heterocyclic group which is as defined above with the exception that $X^4$ represents $NR_7$ or $CH_2$ or an azabicyclic group as defined above.

2. A compound according to claim 1, wherein $R^1$ represents hydrogen.

3. A compound according to claim 1, wherein $R^2$ and $R^3$ are hydrogen.

4. A compound according to claim 1, wherein $R^4$ is an aliphatic group of up to 6 carbon atoms.

5. A compound according to claim 1, wherein $R^4$ is methyl.

6. A compound according to claim 1, wherein $R^5$ represents optionally substituted phenyl or pyridyl.

7. A compound according to claim 1, wherein $R^5$ is substituted by at least one $C_{1-6}$alkyl group.

8. A compound according to claim 1, wherein Aza represents an azabicyclic group.

9. A compound according to claim 1, wherein Aza represents a heterocycloalkyl group.

10. A compound according to claim 1, wherein the heterocycloalkyl group is of formula:

11. A compound according to claim 1, wherein Aza represents a group of formula $NR^9R^{10}$.

12. 1-(5-Azepan-1-yl-1-methyl-2-oxo-2,3,4,5-tetrahydro-1H-benzo[d]azepin-3-yl)-3-m-tolyl-urea, or a pharmaceutically acceptable salt thereof.

13. A pharmaceutical composition containing an effective amount of a compound according to claim 1, together with a pharmaceutically acceptable carrier, diluent or excipient therefor.

14. An intermediate compound of the formula (IA):

where Z represents $NH_2$, NHX where X is an amino protecting group, or —N=C=O, and $R^1$, $R^2$, $R^3$, $R^4$ and Aza are as defined in claim 1.

15. cis-1-(5-Azepan-1-yl-1-methyl-2-oxo-2,3,4,5-tetrahydro-1H-benzo[d]azepin-3-yl)-3-m-tolyl urea.

16. trans-1-(5-Azepan-1-yl-1-methyl-2-oxo-2,3,4,5-tetrahydro-1H-benzo[d]azepin-3-yl)-3-m-tolyl urea.

* * * * *